United States Patent [19]

Patel et al.

[11] Patent Number: 5,624,914
[45] Date of Patent: Apr. 29, 1997

[54] LIPOPHILIC OLIGOSACCHARIDE ANTIBIOTIC SALT COMPOSITIONS

[75] Inventors: Mahesh Patel, Verona; Vincent P. Gullo, Liberty Corner; Roberta Hare, Gilette, all of N.J.; David Loebenberg, Monsey, N.Y.; James B. Morton, Belleville, N.J.; George H. Miller, Montville, N.J.; Heewon Y. Kwon, Edison, N.J.

[73] Assignee: Schering Corporation, Kenilworth, N.J.

[21] Appl. No.: 211,700
[22] PCT Filed: Oct. 14, 1992
[86] PCT No.: PCT/US92/08565
    § 371 Date: Apr. 12, 1994
    § 102(e) Date: Apr. 12, 1994
[51] Int. Cl.$^6$ .................. A61K 31/715; C07G 11/00; C08B 37/16
[52] U.S. Cl. ............... 514/54; 514/58; 536/16.8; 536/103; 536/123.1
[58] Field of Search ............ 514/54, 58; 536/16.8, 536/103, 123.1

[56] References Cited

U.S. PATENT DOCUMENTS

| 3,499,078 | 3/1970 | Luedemann | 424/121 |
| 3,915,956 | 10/1975 | Ganguly et al. | 536/16.8 |
| 3,920,629 | 11/1975 | Ganguly et al. | 536/16.8 |

(List continued on next page.)

FOREIGN PATENT DOCUMENTS

| WO8502767 | 7/1985 | WIPO . |
| WO8702366 | 4/1987 | WIPO . |

OTHER PUBLICATIONS

Ganguly, A. K., et al, Kirk–Othmer, Encyclopedia of Chemical Technology, (1978), 3rd Ed., vol. 2, 205–209.

(List continued on next page.)

Primary Examiner—John Kight
Assistant Examiner—Everett White
Attorney, Agent, or Firm—Thomas D. Hoffman

[57] ABSTRACT

Pharmaceutically acceptable compositions of matter comprising a lipophilic oligosaccharide antibiotic, e.g., the everninomicin-type antibiotic of Formula III, at least a stoichiometric amount of a base, e.g., N-methylglucamine, an amount of, e.g., hydroxypropyl-β-cyclodextrin, and optionally a pharmaceutically acceptable non-ionic surfactant, e.g., Tween-80, pharmaceutical compositions containing such compositions of matter, methods of treating and preventing susceptible bacterial infections in animals especially human beings as well as a method of preventing adverse reaction syndrome while simultaneously delivering an antiinfective amount of a lipophilic oligosaccharide antibiotic such as that of Formula III to said animals as well as the use of the compositions of matter for the preparation of a medicament for such treating or preventing are disclosed.

-continued

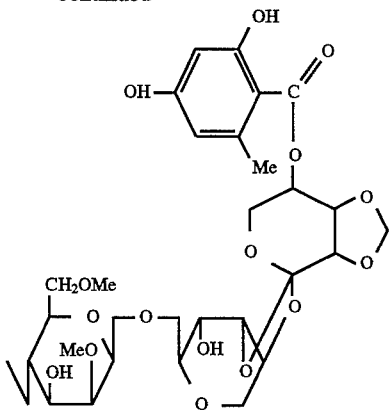

22 Claims, 1 Drawing Sheet

U.S. PATENT DOCUMENTS

| | | | |
|---|---|---|---|
| 3,998,708 | 12/1976 | Kabasakalian et al. | 536/16.8 |
| 4,006,225 | 2/1977 | Ganguly et al. | 536/16.8 |
| 4,027,016 | 5/1977 | Kabasakalian et al. | 536/16.8 |
| 4,129,720 | 12/1978 | Ganguly et al. | 536/16.8 |
| 4,596,795 | 6/1986 | Pitha | 514/58 |
| 4,597,968 | 7/1986 | Waitz | 424/118 |
| 4,622,314 | 11/1986 | Ganguly et al. | 514/54 |
| 4,727,064 | 2/1988 | Pitha | 514/58 |
| 4,735,903 | 4/1988 | Waitz | 435/253 |
| 4,767,748 | 8/1988 | Ganguly et al. | 514/54 |
| 4,870,060 | 9/1989 | Muller | 514/88 |
| 4,983,586 | 1/1991 | Bodor | 514/58 |
| 5,002,935 | 3/1991 | Bodor | 514/58 |
| 5,017,566 | 5/1991 | Bodor | 536/103 |
| 5,024,998 | 6/1991 | Bodor | 536/103 |
| 5,134,127 | 7/1992 | Stella | 536/103 |

OTHER PUBLICATIONS

Girijavallabhan, V.M., + Ganguly, A.K., Kirk–Othmer, Encyclopedia of Chemical Technology (1992) 4th Ed. vol. 3, 259–260.

Ollis, W.D., et al, Tetrahedron (1979) vol. 35, 105–127.

Szejtli, J., Pharmaceutical Technology Jun. 1991, 36–40.

Szejtli, J., Ibid, Pharmaceutical Technology Aug. 1991 24–38.

Pitha, J. The International Journal of Pharmaceutics (1986) 29, 73–82.

Rao, C.T. et al Pharmaceutical Research (1990) vol. 7 (6) 612–615.

Galmarini et al, Tetrahedron (1961) vol. 15, 76–86.

Deulofeu, et al Anales de Quimica (1972) vol. 68, 789.

Mertz, J.L. et al The Journal of Antibiotics (Jul. 1986) vol. 39(7) 877–887.

Ganguly, et al, J. Chem. Soc. chem. Comm. (1980) 56–58.

Ganguly, et al, Heterocycles (1989) vol. 28(1) pp. 83–88.

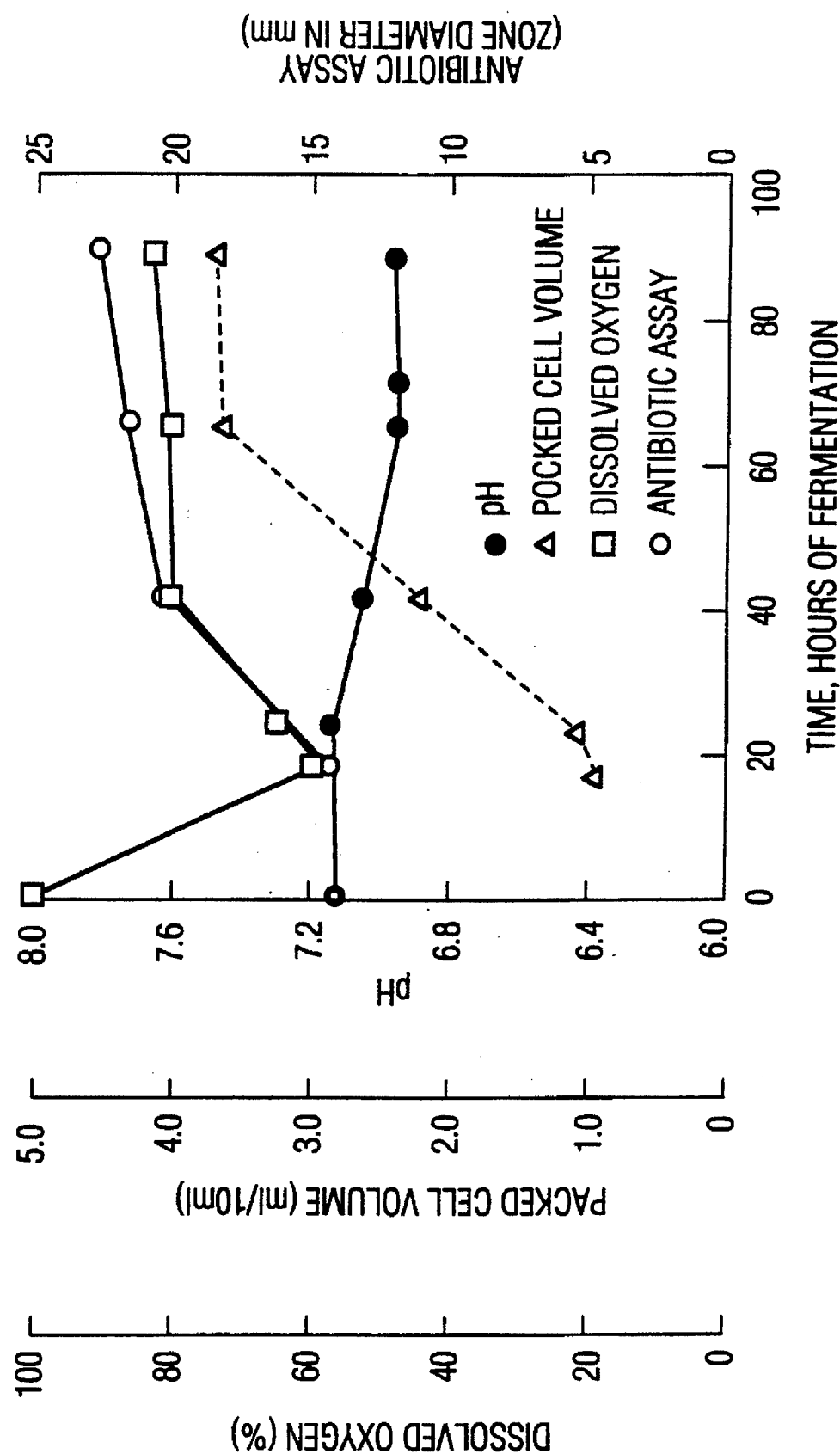
FIGURE

LIPOPHILIC OLIGOSACCHARIDE ANTIBIOTIC SALT COMPOSITIONS

The present application is the U.S. national application corresponding to International Application No, PCT/US 92/08565, filed Oct. 14, 1992 and designating the U.S., which PCT application is in turn a continuation-in-part of U.S. application Ser. No. 07/777,864, filed Oct. 16, 1991, now abandoned.

BACKGROUND OF THE INVENTION

This invention relates to novel compositions of matter comprising a lipophilic oligosaccharide antibiotic, and to pharmaceutical formulations containing such compositions of matter and to methods of making and using such pharmaceutical compositions to treat and/or prevent microbial infections in animals especially mammals such as human beings.

Lipophilic oligosaccharide antibiotics including, for example, everninomicins, curamycins, avilamycins and flambamycins are members of the orthosomycin family of antibiotics which contain at least one acidic phenolic hydrogen, and two orthester linkages associated with carbohydrate residues. See for example. A. K. Ganguly in "Kirk-Othmer, Encyclopedia of Chemical Technology", (1978), Volume 2, pp. 205–209, Third Edition, John Wiley and Sons and W. D. Oillis, et al., *Tetrahedron* (1979), Volume 35, pp. 105–127. These lipophilic oligosaccharide antibiotics exhibit broad spectrum biological activity against gram positive and some gram negative bacteria in various in vitro-assays, and in-vivo activity in animal models such as mice, but to date no pharmaceutically acceptable formulation of such antibiotics useful for vivo administration has been available. Thus, we have observed that injection of these lipophilic oligosaccharide antibiotics cause an adverse reaction syndrome. The term "adverse reaction syndrome" as used herein means symptoms of the following type observed in animals such as mice upon parenteral administration of lipophilic oligosaccharide antibiotics: incoordination, ataxia, lateral recumbency, urination, hind leg rigidity, labored breathing, and arrest. Thus, in summary, there are no known pharmaceutically acceptable compositions of these lipophilic oligosaccharide antibiotics for the safe and effective use of these potent antibiotics in animals including mammals such as human beings.

Cyclodextrins are modified starches made from glucopyranose units and include α-cyclodextrin consisting of six glucopyranose units, β-cyclodextrin consisting of seven glucopyranose units, and γ-cyclodextrin consisting of eight glucopyranose units. The α-, β- and γ-cyclodextrins and derivatives thereof have an inside surface or cavity which is lipophilic and an outer surface which is hydrophilic. This combination of a hydrophobic cavity and a hydrophilic outer surface has led to the use of cyclodextrins and derivatives thereof for the molecular complexation or encapsulation of many hydrophobic and/or unstable drugs of suitable dimensions, thereby improving solubility, stability and bio-availability of such drugs. Derivatives of α-, β- and γ-cyclodextrins for example hydroxypropyl-β-cyclodextdrins are disclosed by Jozsef Szejtli in *Pharmaceutical Technology*, Jun. 1991, 36–40.

Complexes of α-, β- and γ-cyclodextrins, mixtures and derivatives thereof are disclosed in, for example, N. Bodor U.S. Pat. No. 4,983,586. The Bodor U.S. Pat. No. 4,983,586 discloses a method of decreasing the incidence of precipitation of a lipophilic or water labile drug occurring at/or near the injection site and/or in the lungs following parenteral administration, by parenterally administering said drug in an aqueous solution containing a large quantity, i.e., 20 to about 50 weight percent of hydroxypropyl-β-cyclodextrin.

Josef Pitha in U.S. Pat. No. 4,727,064 and *The International J. of Pharmaceutics*, (1986) 29, 73–82 disclose the use of a concentrated, i.e., 40–60 weight percent, aqueous solution of hydroxypropyl-β-cyclodextrin to solubilize various drugs such as acetaminophen, sex steroids, cardiac glycosides such as digoxin, as well as retinoic acid and acid salts thereof. See also the Pitha U.S. Pat. No. 4,596,795 which discloses the administration of the sex hormones, testosterone, progesterone and estradiol as complexes with poly-β-cyclodextrin or hydroxypropyl-β-cyclodextrin.

The Bodor and Pitha references make no reference to phenols or lipophilic oligosaccharide antibiotics.

Janssen Pharmaceutica N. V. International Pat.ent Application No. PCT/EP84/00417 published under International Publication No. WO 85/02767 on 4, Jul. 1985 discloses pharmaceutical compositions comprising complexes of drugs which are unstable or only sparingly soluble in water with partially etherified β-cyclodextrin ("β-CD") of the Formula (β-CD)-OR wherein the residue R is hydroxyethyl, hydroxypropyl, dihydroxypropyl and part of the residue R may optionally be alkyl groups, especially methyl or ethyl.

If the drug molecule has basic or add groups which may possibly be used to increase water solubility by salt formation, the Janssen International Publication No. WO 85/02767 teaches that salt formation as a rule results in decreased efficacy or impaired chemical stability and thus, salt formation to solubilize poorly water soluble acidic and basic compounds is discouraged. There is no disclosure of lipophilic oligosaccharide antibiotics or the compositions of the present invention.

Various strains of bacteria such as gram-positive cocci, e.g., streptococci and enterococci as well as methicillin-resistant and methicillinsusceptible staphylococci have become resistant to commercially available antibiotics, e.g., vancomycin.

Thus, there is a need for pharmaceutically acceptable compositions for treating bacterial infections including methicillin-resistant and methicillin-susceptible staphylococci and vancomycin-resistant bacteria. There is also a need for pharmaceutically acceptable compositions containing a lipophilic oligosaccharide antibiotic active against a broad range of susceptible gram-positive and gram-negative bacterial infections, especially pharmaceutical compositions adapted for parenteral use which avoid occurrence of the adverse reaction syndrome.

BRIEF SUMMARY OF THE INVENTION

Surprisingly, we have discovered a means by which lipophilic oligosaccharide antibiotics having good antibacterial activity against susceptible gram-positive and/or gram-negative bacterial infections may be delivered to animals, especially mammals such as man afflicted with susceptible gram-positive or gram-negative bacterial infections to provide effective treatment and/or prevention thereof while simultaneously avoiding occurrence of the adverse reaction syndrome. This means comprises combining a lipophilic oligosaccharide antibiotic with at least about a stoichiometric amount of a specified base and an amount of an agent such as hydroxypropyl-α-, -β- or -γ-cyclodextrin having about 2 to 15 hydroxypropyl groups per molecule of cyclodextrin sufficient to achieve efficacious delivery of the lipophilic oligosaccharide antibiotic to the serum of an animal while simultaneously avoiding adverse reaction syndrome.

SUMMARY OF THE INVENTION

The present invention provides a composition of matter comprising:

(a) a lipophilic oligosaccharide antibiotic represented by Formula I;

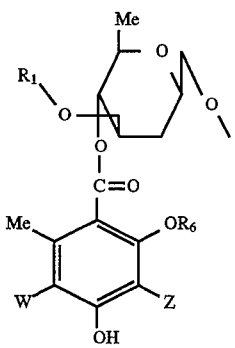

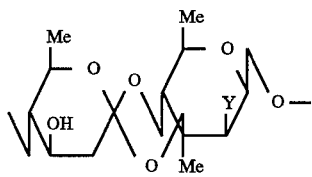

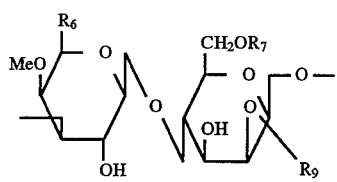

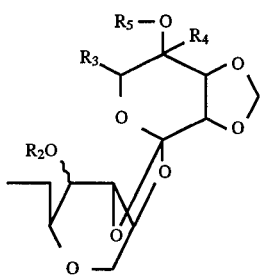

wherein

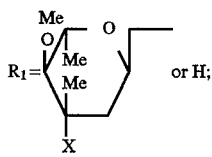

X is one of $NO_2$, NO, $NH_2$, $NHCOCH_3$, NHOH, $NH(C_2H_5)$, $N(C_2H_5)_2$, OH or H;

$R_2$ is one of $=CH_3$, $COCH(CH_3)_2$, $COCH_3$, $CO(CH_2)_3CH_3$, $COCH_2CH_3$ or H;

$R_3$ is $CH_3$ or H;

$R_4$ is one of $COCH_3$, $CH(OCH_3)(CH_3)$, $CH(OH)CH_3$, CHO, or H;

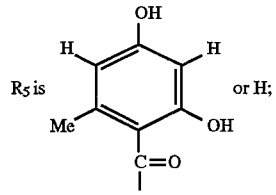

$R_6$ is $CH_3$ or H;

$R_7$ is $CH_3$ or H;

$R_8$ is $CH_3$, $CH_2OH$ or H $R_9$ is $CH_3$ or H;

Y is OH, $CH_3$, or H;

W is Cl or H; and

Z is Cl or H.

(b) at least about a stoichiometric amount of a base capable of forming a pharmaceutically acceptable salt with a lipophilic oligosaccharide antibiotic of Formula I;

(c) an amount of dimethylsulfoxide, glycerol, a sorbitan mono-9-octadecenoate poly(oxy-1,2-ethanediyl) derivative, dextran, a hydroxypropyl-α-, -β- or -γ-cyclodextrin wherein the average number of hydroxypropyl substituents on said and α-, β- and γ-cyclodextrin is in the range of about 2 to about 15, and said amount is sufficient to achieve efficacious delivery of said lipophilic oligosaccharide antibiotic to the serum of an animal while simultaneously avoiding adverse reaction syndrome; and (d) 0 to 6.0% by weight (basis, said antibiotic of Formula I) of a pharmaceutically acceptable non-ionic surfactant.

The present invention more preferably provides a composition of matter comprising (a) a compound represented by the Formula II

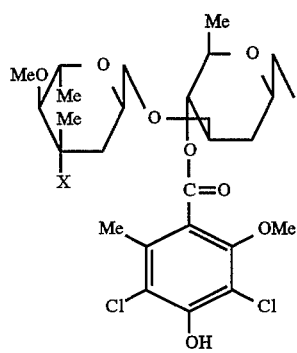

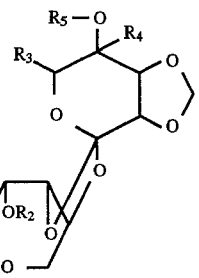

wherein

X is one of $NO_2$, NO, NHOH, $NH_2$, $NHCOCH_3$, $NHC_2H_5$, $N(C_2H_5)_2$, OH or H Y is OH, $CH_3$ or H $R_2$ is H or $CH_3$ $R_3$ is H $R_4$ is H or $CH(OCH_3)(CH_3)$ and $R_5$ is H or
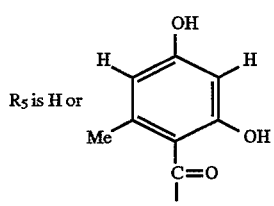

(b) at least about a stoichiometric amount of a base capable of forming a pharmaceutically acceptable salt with a lipophilic oligosaccharide antibiotic of Formula II;

(c) an amount of hydroxypropyl-α-, -β- or -γ-cyclodextrin wherein the average number of hydroxypropyl substituents on said α-, -β- and γ-cyclodextrin is in the range of about 2 to about 15, and said amount is sufficient to achieve efficacious delivery of said lipophilic oligosaccharide antibiotic to the serum of an animal while simultaneously avoiding occurrence of adverse reaction syndrome; and (d) 0 to 6.0% by weight (basis, said antibiotic of Formula II) of a pharmaceutically acceptable non-ionic surfactant.

The present invention further provides a composition of matter comprising (a) the antibiotic compound represented by Formula III

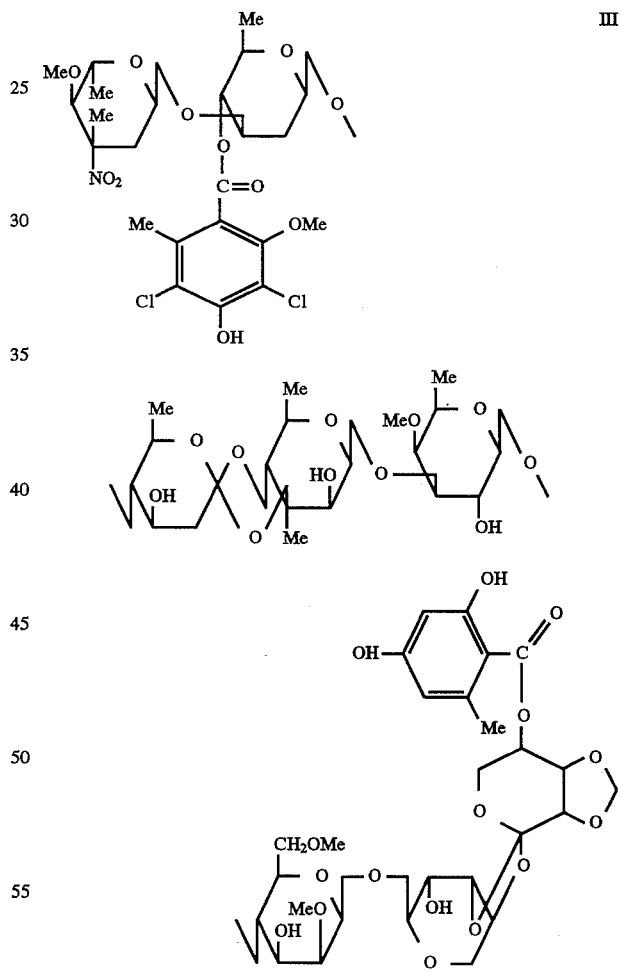

(b) at least about two equivalents of a base (per mole of the compound of Formula III) capable of forming a pharmaceutically acceptable salt of the compound of Formula III (c) an amount of hydroxypropyl-α-, -β- or -γ-cyclodextrin having about 2 to about 15 hydroxypropyl groups per molecule of said -α-, -β- or -γ-cyclodextrin and wherein said amount of said cyclodextrin is sufficient to achieve efficacious delivery of said lipophilic oligosaccharide antibiotic to the serum of an animal while simultaneously avoiding occurrence of adverse reaction syndrome; and (d) 0 to 6.0% by weight (basis, said antibiotic of Formula III) of a pharmaceutically acceptable non-ionic surfactant.

Pharmaceutical compositions formed by admixing a composition of matter comprising a compound represented by Formulas I, II or III and at least about a stoichiometric amount of a base capable of forming a pharmaceutically acceptable salt thereof and an amount of a hydroxypropyl- α-, -β- or -γ-cyclodextrin with a pharmaceutically acceptable carrier as well as methods of using such pharmaceutical compositions for treating or preventing susceptible gram positive and gram negative bacterial infections in animals, especially mammals in need of such treating or preventing are also provided. "The preferred pharmaceutical composition of this invention contains the following: (a) the lipophilic oligosaccharide antibiotic represented by Formula III, (b) a base capable of forming a pharmaceutically acceptable salt with lypophilic oligosacharide antibiotic of Formula III and (c) hydoxypropyl-α-, -β- or -γ-cyclodextrin having about 2 to about 15 hydroxypropyl groups per molecule of said α-, βand γ-cyclodextrin and wherein the molar ratio of (a):(b):(c) is 1:2–3:1–6."

As a preferred form of the invention, the aforesaid pharmaceutical compositions are particularly applicable to parenteral administration, especially in vivo administration to human beings by the intravenous (IV) route.

The present invention also provides a method of preventing adverse reaction syndrome in animals following parenteral injection of a lipophilic oligosaccharide antibiotic represented by Formula I, II or III while simultaneously delivering an antiinfective amount of said antibiotic to an animal, which method comprises parenterally administering to said animal an amount of a composition of matter of this invention sufficient for such purpose together with a pharmaceutically acceptable carrier.

The present invention further provides the use of a lipophilic oligosaccharide antibiotic represented by Formula I for the preparation of a medicament for treating or preventing susceptible gram positive and gram negative bacterial infections in animals, especially mammals in-need of such treating or preventing.

BRIEF DESCRIPTION OF THE FIGURES

FIG. 1 graphically illustrates the progression, with time, of a typical fermentation of *Micromonospora carbonacea*. var. *africana*, NRRL 15099, ATCC 39149.

DETAILED DESCRIPTION OF THE INVENTION AND OF THE PREFERRED EMBODIMENTS

Lipophilic oligosaccharide antibiotics, for example everninomicin antibiotics, exhibit useful in vitro antibacterial activity but do not readily form complete aqueous solutions suitable for safe and effective in vivo administration (i.e. without occurrence of adverse reaction syndrome). Moreover, salts of these antibiotics formed by admixing at least about a stoichiometric amount of a base useful in this invention, e.g. the base, N-methylglucamine ("NMG") do not form complete aqueous solutions, at useful pH values. When said salts were added to water at useful concentrations of salt, we observed that only colloidal dispersions were formed. These colloidal dispersions tended to aggregate, and eventually gelled, especially in the presence of absorbed carbon dioxide and when the pH of such colloidal dispersions was less than about 9.3. We observed that complete aqueous solutions were formed by increasing the molar ratio of NMG to the compound of Formula III from 2:1 or 3:1 up to 12:1, but that the solution so formed with the 12:1 molar ratio had an undesirably high pH, was highly buffered and was irritating. Thus, we observed that parenteral injection into rats or higher primates, such as monkeys of an aqueous formulation containing 12 moles of NMG per one mole of the compound of Formula did not result in adverse reaction syndrome (presumably caused by gelling and precipitation of the compound of Formula III). The formulation, produced irritation upon injection, which irritation is presumably caused by the large amount of NMG base and resulting high pH at the injection site. However, parenteral administration of a composition containing 3 or 5 moles of NMG per mole of the compound of Formula III gave rise to adverse reaction syndrome. Whereas various cyclodextrin agents are known to assist in achieving solutions of specific drugs, (e.g. as the aforementioned Bodor and Pitha references) use of representative agents of this class by themselves failed to achieve the desired result for lipophilic oligosaccharide antibiotics. Thus, for instance, the use of a specific cyclodextrin derivative, and a specific hydroxypropyl-β-cyclodextrin per mole of the everninomicin type antibiotic of Formula III failed to produce a true aqueous solution when used in the ratio of 6 moles of the specific hydroxypropyl-β-cyclodextrin per mole of the everninomicin-type antibiotic of formulation III. Surprisingly, we have found that a composition of matter comprising a lipophilic oligosaccharide antibiotic compound of Formula III, a specified amount of a specific base, e.g., NMG and a specified agent, e.g., hydroxypropyl-β-cyclodextrin in specified amounts provides, when admixed with a pharmaceutically acceptable carriers, especially water, a formulation which may be used safely and effectively for in vivo administration. Surprisingly, we have found that when 1 mole of a lipophilic oligosaccharide antibiotic, e.g., the compound of Formula III was admixed with at least 2 to about 12 moles of a suitable base, e.g., NMG, in water and with 6 moles of a hydroxypropyl-β-cyclodextrin, e.g. , one having about 3 to 7.5 hydroxypropyl groups per molecule of β-cyclodextrin, a clear aqueous solution of the complex (as measured by light scattering nephelometry and line width measurements in the proton NMR; See Example 4) was formed and the parenteral injection of such complexes into animals did not cause adverse reaction syndrome even at high doses, i.e., 800 mg of such complex per kg of body weight. See Table 4.

As will be evident from the in vivo results summarized in Table 1 parenteral injections of the aqueous dispersions of salts, e.g., the NMG salt of the everninomicin-type antibiotic of Formula III into mice and monkeys gave rise to the adverse reaction syndrome. Only when the aqueous solutions of one of the compositions of matter of this invention such as one containing a specified complexing agent, e.g., hydroxypropyl-β-cyclodextrin having about 3 to 7.5 hydroxypropyl groups per molecule of β-cyclodextrin with the NMG everninomicin-type antibiotic of Formula III salts were injected into the animals was the occurrence of adverse reaction syndrome wholly avoided.

Table 2 shows that adverse reaction syndrome can be reduced or completely avoided by parenteral injection into mice of clear aqueous solutions of NMG salts of the everninomicin-type antibiotic of Formula III with the specified, e.g., hydroxypropyl-β-cyclodextrin agents of this invention.

Table 3 illustrates that increasing the molar ratio of base to the everninomicin-type antibiotics of Formula III from 2:1 to 9:1 wholly eliminates the occurrence of adverse reaction syndrome at all concentrations tested upon parenteral injection into mice.

COMPARATIVE EXAMPLE

TABLE 1

THE OCCURRENCE OF ADVERSE REACTION SYNDROME AFTER ADMINISTRATION OF AQUEOUS FORMULATIONS OF ONE MOLE OF THE COMPOUND OF FORMULA III: AND OF 2 MOLES NMG WITH AND WITHOUT HP-β-CD[1]

| Mice (Concentration of III Injected: 80 mg/mL) | % Adverse Reaction Syndrome[2] at the following DOSES (MPK[3]) | | | |
|---|---|---|---|---|
| | 100[3] | 200[3] | 500[3] | 800[3] |
| III[4]: 2NMG | 100 | — | — | — |
| III: 2NMG: 6 HPβCD[5] | 0 | 0 | 0 | 0 |
| Cynomolgus Monkeys (Concentration of III Injected: 50 mg/mL) | | 10[6] | 40[6] | 80[6] |
| III: 2NMG | | 50 | — | — |
| III: 5NMG | | — | 33 | 50 |
| III: 2NMG: 6 HPβCD[5] | | — | 0 | 0 |

Footnotes to Table 1
[1]HP-β-CD is hydroxypropyl-β-cyclodextrin containing 7.4 hydroxypropyl groups per β-CD molecule.
[2]Adverse Reaction Syndrome symptoms were observed in the animals within 2 minutes after IV injection. (single dose)
[3]MPK is mg of drug per kg of body weight of the mice (groups of 5 to 10, CF-1, average weight 20 g, Harlan Sprague - Dawley fasted 18 hours.)
[4]III is the everninomicin-type antibiotic compound represented by Formula III.
[5]Complex formed. See Examples 3 and 4.
[6]MPK is mg of drug per kg of body weight of cynomolgus monkey (weight range 2.9 to 9.6 kg, Schering Corporation Colony, fasted 18 hours). 3 monkeys were used in the 40 MPK, 5NMG experiment; 2 monkeys were used in the other two experiments.

TABLE 2

Adverse Reaction Syndrome (ARS)[1] Upon Administration of Aqueous Formulations of One mole of the Compound of Formula III and 2 Moles of NMG and Selected Additives
% ARS at the following doses (MPK[2]) of Drug of Formula III (20 mg/ml) In Mice

| "Drug of Formula III Injected" | | 100 | 200 | 250 | 300 |
|---|---|---|---|---|---|
| | Tween[3] (Concentration) | | | | |
| III: 2NMG | 0 | 0 | 10 | 100 | 100 |
| III: 2NMG | 0.1% | 10 | 100 | | 100 |
| III: 2NMG | 0.25% | 80 | 100 | | 100 |
| III: 2NMG | 0.5% | 100 | 100 | | 100 |
| III: 2NMG | 1% | 100 | 100 | | 100 |
| III: 2NMG | 2% | — | 0 | 0 | 40 |
| III: 2NMG | 3% | 0 | 0 | 0 | 0 |
| | DMSO[4] (Concentration) | | | | |
| III: 2NMG | 0 | 0 | 0 | 90 | 100 |
| III: 2NMG | 1% | 0 | 40 | 100 | 100 |
| III: 2NMG | 5% | 0 | 10 | 20 | 50 |

TABLE 2-continued

Adverse Reaction Syndrome (ARS)[1] Upon Administration of Aqueous Formulations of One mole of the Compound of Formula III and 2 Moles of NMG and Selected Additives
% ARS at the following doses (MPK[2]) of Drug of Formula III (20 mg/ml) In Mice

| "Drug of Formula III Injected" | | 100 | 200 | 250 | 300 |
|---|---|---|---|---|---|
| III: 2NMG | 10% Glycerol (Concentration) | 0 | 0 | 10 | 50 |
| III: 2NMG | 0 | 0 | 0 | 100 | 100 |
| III: 2NMG | 5% | 0 | 90 | 90 | 100 |
| III: 2NMG | 10% Dextran 40[5] (Concentration) | 0 | 60 | 100 | 100 |
| III: 2NMG | 0 | 0 | 0 | 100 | — |
| III: 2NMG | 1% | 20 | 100 | | — |
| III: 2NMG | 10% Dextran 70[6] (Concentration) | 0 | 50 | 70 | 100 |
| III: 2NMG | 6% HPβCD[7] (Molar Ratio) | 0 | 90 | 100 | — |
| III: 2NMG | 0 | 0 | 0 | 100 | 100 |
| III: 2NMG | 1:0.5 | | 0 | | 50 |
| III: 2NMG | 1:1.5 | | 0 | | 60 |
| III: 2NMG | 1:2.5 | | 0 | | 30 |
| III: 2NMG | 1:3 | | 0 | | 10 |
| III: 2NMG | 1:3 | | | | 10 |
| III: 2NMG | 1:6 | | | | 0 |

Footnotes to TABLE 2
[1]Adverse Reaction Syndrome Symptoms observed in the mice (groups of 5 to 10, CF-1, average weight 20 g, Harlan Sprague Dawley fasted 18 hours) within 2 minutes after IV injection. (single dose)
[2]MPK is mg of drug per kg of animal body weight.
[3]Tween is Sorbatan mono-9-octadecanoate poly (oxy-1,2-ethanediyl) or as Polysorbate 80 available from ICI Americas Inc., Wilmington Delaware under the tradename Tween 80.
[4]DMSO is dimethyl sulfoxide
[5]Dextran 40 is a high molecular weight (40,000) polymer of glucose available from Sigma Chemical.
[6]Dextran 70 is a high molecular weight (70,000) polymer of glycose available from Sigma Chemical.
[7]HPβCD is hydroxypropyl-β-cyclodexdrin having 7.4 hydroxypropyl groups per molecule of CD.

TABLE 3

Effect of Concentration of Lipophilic Oligosaccharide Antibiotic NMG Salt and Molar ratio of NMG to Antibiotic upon Adverse Reaction Syndrome[1] in Mice

| Drug of Formula III | % ARS[1] at the following doses (MPK[2]): | | | | |
|---|---|---|---|---|---|
| (Drug Concentration) | 50 | 100 | 200 | 300 | 400 |
| III[3]: 2NMG (10 mg/ml) | — | — | 50 | — | — |
| III: 2NMG (20 mg/ml) | — | 20 | 100 | — | — |
| III: 2NMG (50 mg/ml) | 70 | 100 | — | — | — |
| III: 3NMG (20 mg/ml) | — | — | 0 | 0 | 20 |
| III: 3NMG (40 mg/ml) | — | — | 0 | 15 | 40 |
| III: 3NMG (80 mg/ml) | — | — | 100 | — | — |
| III: 5NMG (20 mg/ml) | — | — | 0 | 0 | — |
| III: 5NMG | — | — | 0 | — | 40 |

TABLE 3-continued

Effect of Concentration of Lipophilic Oligosaccharide Antibiotic NMG Salt and Molar ratio of NMG to Antibiotic upon Adverse Reaction Syndrome[1] in Mice

| Drug of Formula III | % ARS[1] at the following doses (MPK[2]): | | | | |
|---|---|---|---|---|---|
| (Drug Concentration) | 50 | 100 | 200 | 300 | 400 |
| (50 mg/ml) III: 9NMG | — | — | 0 | 0 | 0 |
| (20 mg/ml) III: 9NMG | — | — | 0 | 0 | 0 |
| (40 mg/ml) III: 9NMG | — | — | 0 | — | 0 |
| (80 mg/ml) | | | | | |

Footnotes to Table 3
[1]Adverse Reaction Syndrome Symptoms observed in mice (groups of 5 to 10, CF-1, average weight 20 g, Harlan Sprague Dawley, fasted 18 hours) within 2 minutes after IV injection. (single dose)
[2]MPK is mg of the drug of Formula III per kg of body weight.
[3]III is eveninomicin-type antibiotic compound represented by Formula III.

Perhaps even more surprisingly, we observed that the Minimum Inhibitory Concentrations ("MIC") in the in vitro models, and the 50% protective dose ("PD$_{50}$") values in an in vivo mouse protection model, of the complex of 3 to 6 moles of hydroxypropyl-β-cyclodextrin "HPβCD" in combination with one mole of the compound of Formula III and 2 or 3 moles of NMG were essentially the same as the MICs and PD$_{50}$ values for the compound of Formula III and for those of the NMG salt of the compound of Formula III with HPβCD in said models. The protein binding values for the complex of 2 or 3 moles of NMG per of the compound of Formula III with 6 moles of HPβCD remained-at 96–98% of the binding values that we observed for the salt of the compound of Formula III with 2 moles of NMG.

Thus, we have surprisingly discovered pharmaceutically acceptable compositions of matter containing a lipophilic oligosaccharide antibiotic which allows effective delivery of such antibiotic to the serum of an animal such as a mammal especially a man afflicted with a bacterial infection susceptible to treatment by such lipophilic oligosaccharide antibiotic of Formulas I, II and III.

The 2-hydroxypropyl derivatives of α-, β- and γ-cyclodextrin useful in the present invention have about 2 to 11 hydroxypropyl groups per molecule of cyclodextrin and are readily prepared by reacting one of α, β- or γ-cyclodextrin with 1,2-propylene oxide in the presence of base in a manner to yield multicomponent, amorphous mixtures such as described by J. Pitha in U.S. Pat. No. 4,727,064, J. Pitha, et al., in *International Journal of Pharmaceutics* (1986), 29. 73–82 or by Muller in U.S. Pat. No. 4,870,060. The self condensation products of propylene oxide are removed and the degree of substitution, i.e., number of the hydroxypropyl groups per molecule of cyclodextrin are conveniently determined by proton nuclear magnetic resonance and/or mass spectroscopy in accordance with the methods described by Pitha in U.S. Pat. No. 4,727,064 and *International Journal of Pharmaceutics* (1986) 29. 73–82 or C. T. Ras, et al. in *Pharmaceutical Research* (1990) 7, (No. 6) 612–615. The 2-hydroxypropyl-α-, -β- and -γ-cyclodextrins having about 2 to 15, preferably about 3 to 9, more preferably about 5–7.5 hydroxypropyl groups per molecule of α-, -β- and -γ-cyclodextrin are readily prepared by conventional procedures and are also available commercially from Cyclolab, a wholly owned subsidary of CHINOIN, Pharmaceutical and Chemical Works. Ltd., 1325 Budapest, Hungary; Walker-Chemie GmbH, Division L. Biotechnology Prinzregentenstraβe 22 D-8000, Munchen 22 West Germany; American Maize, Hammond, Ind.; Pharmatec Inc, P.O. Box 730, Alachua Fla. 32615 and Janssen, Biotech N.V. Lammerdries 55, B-2430 Olen, Belgium.

The amounts of such hydroxypropyl-α-, -β- and -γ-cyclodextrins sufficient to achieve efficacious delivery of the lipophilic oligosaccharide antibiotic to the serum of an animal, especially a human being, without causing the adverse reaction syndrome upon injection of a pharmaceutical composition containing a lipophilic oligosaccharide antibiotic of Formula I, II or III, at least a stoichiometric amount of a selected base and an amount of a hydroxypropyl-α-, -β- or -γ-cyclodextrin in accordance with this invention are given in the paragraph hereinbelow.

Such an amount of hydroxypropyl-β-cyclodextrin ("HP-α-CD") is about 5 to 15 moles of HP-α-CD per mole of a lipophilic oligosaccharide antibiotic of Formula I. Such an amount-of hydroxypropyl-β-cyclodextrin (HPβ-CD) is about 1–9, preferably about 2–6, moles of HP-β-CD per mole of a lipophilic oligosacchide antibiotic of Formula II or III; such an amount of hydroxypropyl-γ-cyclodextrin ("HP-γ-CD") is about 2–8 moles, preferably about 3–5 moles of HP-γ-CD per mole of a lipophilic oligosaccharide antibiotic of Formula I. The salts of the lipophilic oligosaccharide antibiotic represented by Formula III are uniquely suitable for forming complete solutions in water with a broad range of hydroxypropyl-α-, -β- and -γ-cyclodextrins having from about 2 to 15 hydroxypropyl groups per molecule of HP-α-CD or HP-β-CD or HP-γ-CD. As shown in Table 4, a broad range of HP-β-CDs containing from 3.9 to 7.5 hydroxypropyl groups per HP-β-CD molecule essentially prevented adverse reaction syndrome upon parenteral injection into a mouse model of a complex of one mole of the compound of Formula III and 2 moles of NMG and 6 moles of HP-β-CD.

TABLE 4

Adverse Reaction Syndrome[1] upon Parenteral Injection (800 MPK, 80 mg of the compound of Formula III per ml) into Mice of an Aqueous Solution Complexes of One Mole of the Compound of Formula III and Two Moles of NMG and Six Moles of HP-β-CD having from 3.9 to 7.5 Hydroxypropyl Groups

| Number of Hydroxypropyl Groups per molecule of HP-β-CD | % Adverse Reaction Syndrome |
|---|---|
| No HP-β-CD | 90 |
| 7.4 | 0 |
| 7.5 | 0 |
| 7.4 | 0 |
| 7.4 | 0 |
| 7.2 | 0 |
| 6.9 | 0 |
| 6.7 | 10 |
| 6.3 | 0 |
| 6.2 | 0 |
| 5.2 | 0 |
| 4.5 | 0 |
| 4.4 | 0 |
| 4.1 | 10 |
| 3.9 | 0 |

[1]Adverse Reaction Syndrome observed in mice (groups of 10 CF-1, average weight 20 g, Harlan Sprague Dawley, fasted 18 hours) within 2 minutes after IV injection. (single dose)

In the course of development of the compositions of matter of this invention, we prepared such compositions by addition of a lipophilic oligosaccharide antibiotic, e.g., the compound represented by Formula III to at least a stoichiometric amount, e.g., about 2 to 3 moles of the preferred base, N-methyl glucamine and a sufficient amount of dimethylsulfoxide or glycerol or of sorbitan mono-9-octadecenoate poly (oxy-1,2-ethanediyl) derivatives, e.g., polysorbate 80 or Tween 80, or a dextran such as Dextrans 40 or 70 brands of polysaccharides [produced by action of bacteria growing on sucrose substrate containing a backbone of D-glucose units linked predominantly α-D (1→6). Dextran 40 and 70 (average molecular weight of 40,000 and 70,000, respectively) are polysaccharides produced by the action of L. mesenteroxides on sucrose; such sufficient amounts of dimethyl sulfoxide, glycerol, polysorbate 80 or a dextran were found to achieve efficacious delivery of said lipophilic oligosaccharide antibiotics to the serum of an animal while simultaneously reducing or avoiding occurrence of adverse reaction syndrome. Reference is made to the results in Table 2. Increasing the amount of DMSO and glycerol [to 10 weight percent] reduced the occurrence of adverse reaction syndrome; the sufficient amounts of DMSO and glycerol are about 5 to 10 weight percent and about 10 weight percent, respectively. Increasing the amount Dextrans 40 and 70 also reduced the occurrence of adverse reaction syndrom; such sufficient amounts of Dextran 40 and Dextran 70 are about 2–10, and at least about 6 weight percent respectively. Amounts of Tween 80 from about 0.1 weight percent to about 1 weight percent increased occurrence of adverse reaction syndrome but amounts of Tween 80 greater than 1 weight percent decreased occurrence of adverse reaction syndrome while amounts of Tween 80 greater than about 2 to about 3 weight percent resulted in almost complete avoidance of adverse reaction syndrome. Amounts of Tween 80 greater than 2 to about 3 weight percent are Considered sufficient (all weight percents are based the total weight of the composition). However, the use of hydroxyl propyl-α-, -β- or γ-cyclodextrins is preferred for the pharmaceutically acceptable compositions of this invention. See Table 2 hereinabove.

The bases found suitable for use in the present invention are those which form pharmaceutically acceptable salts of the lipophilic oligosaccharide antibiotics of Formulas I, II or III and include suitable organic and inorganic bases. Suitable organic bases include primary, secondary and tertiary alkyl amines, alkanolamines, aromatic amines, alkylaromatic amines and cyclic amines. Exemplary organic amines include the pharmaceutically acceptable bases selected form chloroprocaine, procaine, piperazine, glucamine, N-methylglucamine, N,N-dimethyl glucamine ethylenediamine. diethanolamine, diisopropylamine, diethylamine, N-benzyl-2-phenylethylamine, N-N'-dibenzylethylenediamine, choline, clemizole, tris (hydroxymethyl)aminomethane, or D-glucosamine. The preferred organic bases include N-methyl glucamine ("NMG"), diethanolamine, and tris(hydroxymethyl) aminomethane ("TRIS"). Use of NMG in this invention is more preferred. See Tables 2 and 3. The suitable inorganic bases include alkali metal hydroxides such as sodium hydroxide. The bases found useful in the preparation of compositions of matter of the present invention produce aqueous solutions having a pH of at least about 9.3. Lysine forms aqueous solutions having a pH of less than 9.3 and thus lysine is not a suitable base for the present invention. Divalent metal hydroxides such as the alkaline earth hydroxides, calcium hydroxide and barium hydroxide did not form aqueous solutions of the lipophilic oliogosaccharide antibiotics of Formulas I, II or III in the presence of 6 moles of HP-β-CD having a pH of at least about 9.3 and were unacceptable as bases for use in the present invention.

The term "at least about a stoichiometric amount" as used herein in reference to the bases Useful in this invention means the amount of base needed to substantially completely react with (i.e. result in more than 99% complete reaction) the acidic phenolic hydrogens of the lipophilic oligosaccharides antibiotics of Formulas I, II, III having one or two or three phenolic hydrogens. (Compound of Formula III has three phenolic hydrogens of which only two are acidic). For the compounds of Formulas and II wherein $R_5$=H, there is only one phenolic acidic hydrogen per molecule and the stoichiometric amount of the pharmaceutically acceptable bases of this invention is at least about one mole of such base up to 12 moles of such bases. For the compounds represented by Formula I and II wherein

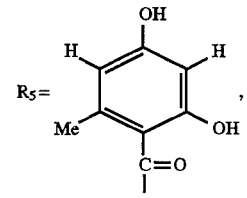

and for the compounds of Formula III there are two acidic phenolic hydrogens per mole of such compounds, the stoichiometric amount of base required to completely react with the two acidic phenolic hydrogens is at least 2 up to about 12 moles of the pharmaceutically acceptable bases useful in this invention. For the preferred lipophilic oligosaccharide antibiotics of Formula I, and II wherein

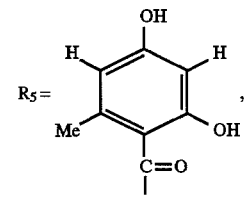

and those of Formula III, it is preferred to use about 2 to 6 moles, and it is more preferred to use about 2.0 to 3.5 moles and most preferred to use about 2 to about 3 moles of a pharmaceutically acceptable base such as NMG to maintain the pH of an aqueous solution thereof at a value of about 9.3 as opposed to solutions having a higher pH, and which solutions were highly buffered widen 6–12 moles of NMG were used.

The term "lipophilic oligosaccharide antibiotic" as used herein means selected lipophilic members of the orthosomycin family of antibiotics, more particularly fiambamycin, the everninomicins, everninomicin-type antibiotics, curamycin and the avilamycin A-N antibiotics Flambamycin, a lipophilic oligosaccharide antibiotic produced by *Streptomyces hygroscoicus* DS 23230, whose structural Formula is that of Formula I wherein $R_1$=$R_5$=H, Y=OH, $R_2$=COCH(CH$_3$)$_2$, $R_3$=$R_6$=$R_7$=$R_8$=$R_9$=CH$_3$, $R_4$=COCH$_3$ and W=Z=Cl is disclosed by W. D. Ollis in *Tetrahedron*, (1979), 35, 105–127.

Curamycin A is a flambamycin antibiotic (having a structural Formula represented by Formula I wherein $R_1$, $R_3$, $R_4$, $R_5$, $R_6$, $R_7$, $R_8$, $R_9$, W and Z are the same as for flambamycin except $R_2$=COCH$_3$ and Y=H. See O. L. Galamarine et al. *Tetrahedron* (1961), 15, 76 and V,. Deulofer et al., *Anales de Quimica* (1972), 68, 789.

Avilamycin A-N antibiotics are lipophilic oligosaccharide antibiotics isolated from an antibiotic complex produced by cultures of the organism *Streptomyces viridochromogenes*, NRRL 2860. See J. L. Mertz et al. *The Journal of Antibiotics* (July 1986) Vol. 39 (No. 7) 877–887. The structural Formulas for the avilamycin A-N antibiotics are represented by Formula I wherein, $R_1=R_5=H$, $Y=H$, $R_2=COCH(CH_3)_2$, $COCH_3$, $CO(CH_2)_3CH_3$, $COCH_2CH_3$ or H, $R_3=CH_3$, $R_4=COCH_3$, $CH(OH)CH_3$ or CHO and $R_6=CH_3$ or H; $R_7=CH_3$ or H; $R_8=CH_3$, $CH_2OH$ or H; $R_9=CH_3$ or H and W=H or Cl and Z=Cl.

The everninomicin antibiotics useful in this invention include the everninomicins B, C and D isolated from the antibiotic complex produced by the organism, *Micromonospora carbonacea* var. *carbonacea* NRRL 2972 and a variety thereof *M. carbonacea* var. *aurantiaca* NRRL 2997 as described in U.S. Pat. No. 3,499,078. The everninomicin derivatives having a nitroso, hydroxylamino or amino moiety in place of the nitro moiety in everninomicins B, C and D may be obtained by reduction of the nitro moiety in everninomicins B, C and D in accordance with the procedures of U.S. Pat. No. 4,006,225. A preferred everninomicin is N-acetylaminoeverninomicin-D and is represented by Formula II wherein $X=NHCOCH_3$, $Y=H$; $R_4=CH(OCH_3)(CH_3)$; $R_3=R_5=H$ and $R_2=CH_3$. N-acetylaminoeverninomicin-D and its di N-methylglucamine salt may be prepared by the procedures of U.S. Pat. No. 4,129,720 which discloses reduction of the nitro moiety of everninomicins B, C and D to produce the amino derivatives which are subsequently convened into the N-acyl e.g. N-acetyl, N-alkyl, e.g. $NH(C_2H_5)$, or N,N-dialkyl, e.g. $N(C_2H_5)_2$, derivatives. The preparation of the N-acyl-N-hydroxylamino everninomicin B, C and D derivatives and pharmaceutically acceptable salts thereof are also described. The preparation of everninomicin 7 represented by Formula II wherein $X=OH$, $Y=H$, $R_4=CH(OCH_3)(CH_3)$, $R_5=H$ and $R_2=CH_3$ is disclosed by A. K. Ganguly et al. in *J. Chem. Soc., Chem. Corem.* 1980, 56–58.

The "everninomicin-type" antibiotics are those lipophilic oligosaccharide antibiotics represented by Formula II wherein $X=NO_2$, NO $NH_2$, OH, $NHCOCH_3$, $NHC_2H_5$, $N(C_2H_5)_2$, NHOH or H, Y=OH, $R_2=CH_3$ or H; $R_3=H$, $R_4=CH(OCH_3)(CH_3)$ or H and

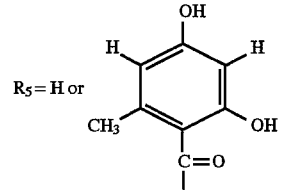

The compounds of Formula II wherein $X=NO_2$ or $NH_2$, Y=OH $R_2=R_3=R_4=H$, and

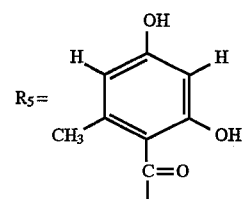

are isolated from an antibiotic 13-384 complex produced by fermentation of the organism *Micromonospora carbonacea* var. *africana*, NRRL 15099, ATCC 39149. Antibiotic components 1 (Formula II, $X=NO_2$ and Y, $R_2$, $R_3$, $R_4$ and $R_5$ are each defined as hereinabove in reference to antibiotic 13-384) and 5 (Formula II, $X=NH_2$ and Y, $R_2$, $R_3$, $R_4$, and $R_5$ are as defined as hereinabove in reference to antibiotic 13-384) disclosed n U.S. Pat. No. 4,597,968 and 4,735,903 have the structural Formulas disclosed by AK Ganguly et al. in *Heterocycles* (1984) Vol. 28 (No. 1) p 83–88. The everninomicin-type antibiotics of Formula II wherein $X=H$, NHOH, $NHCOCH_3$ and acyl and alkyl derivatives thereof are described in U.S. Pat. No. 4,622,314 and 4,767,748.

The preferred compositions of matter of this invention include compounds of Formula II wherein $R_3=H$,

| and | X | Y | $R_4$ | $R_5$ | $R_2$ |
|---|---|---|---|---|---|
| | $NO_2$ | OH | $CH(OCH_3)(CH_3)$ | H | $CH_3$ |
| | OH | H | " | " | " |
| | $NO_2$ | H | H | " | " |
| | $NO_2$ | H | $CH(OCH_3)(CH_3)$ | " | " |
| | $NHCOCH_3$ | H | " | " | " |
| | $NO_2$ | OH | H | (structure) | H |
| | H | " | " | " | " |
| | NHOH | " | " | " | " |
| | $NHCOCH_3$ | " | " | " | " |
| | $NH_2$ | " | " | " | " |
| | $NHC_2H_5$ | " | " | " | " |
| | $N(C_2H_5)_2$ | " | " | " | " |

The most preferred everninomicin-type antibiotic is named 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) having the molecular Formula of: $C_{70}H_{97}NO_{38}Cl_2$ and the molecular weight of 1629 and is represented by Formula III.

The preferred compound of the Formula III may be obtained by fermentation of *Micromonospora carbonacea* var. *africana* NRRL 15099, ATCC 39149 or, more preferably, by an improved strain thereof, obtained as hereinafter described.

Utilizing the strain SCC 1413 of the culture NRRL 15099, ATCC 39149, the preferred compound of the Formula III may suitably be obtained by the procedures outlined in Example 1 of U.S. Pat. No. 4,597,968. In a specific example, in accordance with this procedure, the initial stage inoculum for the fermentation of strain SCC 1413 was prepared by transferring 2.5 ml of a frozen whole broth of 50 ml of the germination medium in 250 ml Erlenmeyer flasks. The germination medium consisted of beef extract, 0.3%; tryptone, 0.5%; dextrose, 0.1%; potato starch, 2.43%; yeast extract, 0.5%; and calcium carbonate, 0.2%. The pH of the medium was adjusted to 7.5 prior to sterilization. The flasks were incubated at 30° C. on a gyratory shaker at 250 r.p.m. for 48 hours. For the second stage germination, 2 liter Erlenmeyer flasks containing 500 ml of the same medium were inoculated with a 5% volume of the first stage germination. The conditions for incubation were the same as before. A third inoculum stage was employed for all stirred tank fermentations and was prepared by a 24 hour incubation of the culture under the same conditions as employed for the second stage.

Ten liter fermentations were initially carried out in 14 liter NBS Laboratory Fermentors in a fermentation medium containing yeast extract, 0.5%; casein hydrolysate, 0.5%; cerelose, 1%; soluble starch, 2.0%; calcium carbonate, 0.4%; and cobalt chloride, 0.24 mg %. The pH of the medium was adjusted to 6.7 before sterilization and to 7.0 before inoculation. The third stage inoculum (22.5%) was used to initiate the fermentation which was conducted at 30° C. with 0.35 vvm of air and 350 rpm agitation.

During the course of the fermentation, antibiotic production was monitored every 24 hours by bioassay of the whole broth against *Staphylococus aureus* 209 P (pH of the agar, 7.0) and *Escherichia coli* ATCC 10536 (pH of the agar, 8.0). The growth of the producing organism (packed cell volume ), pH and dissolved oxygen levels were also determined either intermittently or continuously. The course of a typical 10 liter tank fermentation is illustrated in FIG. 1.

We have developed an improved strain from SCC1413, NRRL 15099, ATCC 39149 using standard mutagenesis agents and obtained strains producing improved yields of the preferred everninomicin-type antibiotic compound of the Formula III. In a specific example, the parent strain SCC 1413, NRRL 15099, ATCC 39149 was exposed to an amount of the mutagenesis agent, N-nitrosoguanidine (NTG) sufficient to kill 90% of a culture of SCC 1413, ATCC 39149, NRRL 15099. Fifteen hundred surviving isolates were examined for-enhanced biological activity against *S. aureus* and *E. coli* to determine which isolates exhibited improved production of the desired antibiotic of Formula III. The test procedure employed to determine enhanced activity was as follows: Single colony isolates were germinated in test tubes containing 10 ml of germination media of Example 1 of U.S. Pat. No. 4,597,968 and shaken at 250 r.p.m. on a gyratory shaker at 30° C. for 48 hours. Fermentation studies were initiated by transferring 2.5 ml of the seed to 250 ml Erlenmeyer flasks containing 50 ml of fermentation media and incubating at 30° C. for 96 hours at 250 r.p.m. on a gyratory shaker. The antibiotic obtained following fermentation was then assayed for improved antibiotic production by assessing the activity against *S. aureus* and *E. coli* and isolates giving improved yields of the desired antibiotic were identified. The results for a representative improved isolate, designated herein as strain SCC 1631, are given in Table 5.

The foregoing strain-development procedure was repeated by subjecting the representative improved isolate, SCC 1631, to a further exposure to NTG, again in an amount sufficient to kill 90% of the cultures, followed by selection of the isolates on agar plates containing 150 µg/mL of everninomicin D. Isolates giving enhanced production of the desired antibiotic were again selected by assessing biological activity thereof against *S. aureu* and *E. coli*. One such isolate, herein designated strain SCC 1756, was then utilized to produce the preferred antibiotic of Formula III.

Further, NTG mutagenesis of SCC 1756 yielded our current production strain, SCC 2146.

In the foregoing mutation procedures, the protocols for both studies were as previously described hereinabove. For the latter two mutation studies, fermentation broths were extracted with ethyl acetate and the concentrates were chromatographer on Whatman LKGDF thin layer plates in a solvent system consisting of chloroform:methanol (9:1 v/v) followed by bioautography against *S. aureus* and *E. coli* to confirm the production of all components of the antibiotic complex. To follow increased titers of the compound of Formula III, thin layer plates were examined by using the Shimadzu CS-930 TLC plate scanner and quantitating the higher producing extracts by using HPLC. Combined titers are defined as the sum of the compound of Formula III (antibiotic 13-384, component 1 of U.S. Pat. No. 4,597,968) and the nitroso analog of said component 1, i.e., antibiotic 13-384, component 1a.

Early observations indicated that although the parent strain SCC 1413 grew rapidly at 34° C., antibiotic production was optimal if the temperature was lower. This phenomenon was investigated as a means of fermentation optimization. Results of the temperature study indicated that optimal production was obtained when the temperature was lowered from 34° C. to 30° C. after 24 hours of incubation. All subsequent work in stirred tanks followed the protocol of incubating the fermentation at 34° C. for 24 hours followed by lowering the temperature to 30° C. for the duration of the fermentation run.

Media studies were conducted in conjunction with the isolation of the improved production strains. Carbon and nitrogen source substitutions were investigated as well as the addition of minerals and other complex nutrients. Replacement of casein hydrolysate by either meat or fish peptone and substituting potato dextrin (PDP 650) for soluble starch enhanced antibiotic production using strains SCC 1413 and SCC 1631. Subsequent enhancements in the production of the compound of Formula III were observed with the addition of corn steep liquor and nickel (II) chloride in studies with strain SCC 1756. The current production fermentation media (4I+½ Ni) optimized for the compound of Formula III contains glucose, 2.2 weight %; PDP 650 dextrin, 4.0 weight %; yeast extract, 0.5 weight %; meat peptone, 0.6 weight %; corn steep liquor, 0.5% vol., nickel chloride, $2.5\times10^{-6}$M; and calcium carbonate, 0.4 weight %. The pH of the medium was adjusted to 6.7 before the addition of calcium carbonate. Table 6 shows a comparison of the titers for strains SCC 1413, SCC 1631, SCC 1756 and SCC 2146 obtained in shake flask studies (50 ml of the current production medium in 250 ml erlenmeyer flasks, at 30° C., for 96 hours, at 300 r.p.m.). The marked titer improvement (15 fold over the original parent, SCC 1413)is clearly demonstrated. Titers of 555–750 ug/ml (sum of the compound of Formula III and the nitroso derivative thereof) have been achieved in 100 liter fermentations using the current production medium with our best production strain. SCC 2146 (Table 7).

TABLE 5

Comparison of Strains SCC 1413 and SCC 1631 in Fermentations Showing, Zones of Inhibition (mm) on Agar Plates[1]

| Strain | TEST 1 | | | TEST 2 | | |
|---|---|---|---|---|---|---|
| | S. aureus pH 7 | | E. coli pH 8 | S. aureus pH 7 | | E. coli pH 8 |
| SCC | Undil. | 1:20 | Undil. | Undil. | 1:20 | Undil. |
| 1631 | 28.7, 28.7 | 22.0 | 20, 17.5 | 28.1, 28.8 | 23.3, 23.1 | 14.8 C[2], 15.0 C[2] |
| 1413 | 28.7, 28.7 | 19.0 | 12 H[3], 12H[3] | 23.8, 23.1 | 20.5, 19.8 | 12 H[3], 12 H[3] |

[1]Duplicate Determinations Where Appropriate
[2]Clear Zone
[3]Hazy Zone

TABLE 6

Flask Comparison of SCC's 1413, 1631, 1756 and 2146 Strains of Micromonospore Carbonacea var africana NRRL 15099, ATCC 39149
Titer of the compound of Formula III and Nitroso Analog (1A) Thereof (μg/ml)

| Culture | 1 (NO$_2$) | 1a (NO) | combined (1 + 1a) |
|---|---|---|---|
| SCC 1413 | 5 | 3 | 8 |
| SCC 1631 | 14 | 4 | 18 |
| SCC 1756 | 17 | 16 | 33 |
| SCC 2146 | 39 | 85 | 124 |

TABLE 7

100 Liter Fermentations of SCC 2146
Titer of Formula III and the NO Analog (1A) Thereof (μg/ml)

| Media | 1 (NO$_2$)[1] | 1a (NO[2]) | combined (1 + 1a) |
|---|---|---|---|
| 4I | 105 | 315 | 420 |
| 4I | 135 | 170 | 305 |
| 4I + ½Ni[3] | 55 | 500 | 555 |
| 4I + Ni[4] | 150 | 575 | 725 |
| 4I + ½Ni[3] | 100 | 650 | 750 |
| 4I + ½Ni[3] | 130 | 470 | 600 |

Footnotes to Table 7
[1]The everninomicin-type antibiotic of Formula III.
[2]The Nitroso analog of the antibiotic of Formula III.
[3]Nickel concentration (½ Ni) = $2.5 \times 10^{-6}$ M.
4Nickel concentration Ni = $5 \times 10^{-6}$ M The isolation of the lipophilic oligosaccharide antibiotic complex containing the compound of Formula III and the nitroso analog thereof was accomplished by use of the procedures of Example 1C of U.S. Pat. No. 4,597,968. The fermentation broth was adjusted to pH 7 and extracted twice with a volume of ethyl acetate two times the volume of the fermentation broth. The combined ethyl acetate extracts were concentrated and the amounts of the compound of Formula III and the nitroso analog thereof were determined by HPLC, The nitroso analog was convened into the nitro compound of Formula III by use of an oxidizing agent such as tertiary butyl hydroperoxide (t-BuO$_2$H) with vanadyl acetylacetonate dissolved in an aprotic organic solvent at room temperature. The course of the reaction was monitored by, for example, HPLC. The reaction mixture was quenched with trialkylphosphite and the crude product was purified by standard chromatographic techniques. e.g. silica gel column chromatography (acetone/CH$_2$Cl$_2$) or a column containing a polyhydroxyvinyl polymer such as Fractogel (Toyo Pearl) available from Toyo Haas, Philadelphia, Pa.

The pharmaceutically acceptable conposition of matter of this invention may contain, in addition to (a) an antibiotic of Formula I, II, III , (b) a base capable of forming a pharmaceutically acceptable salt of such antibiotics and (c) an a specified amount of, for example, hydroxypropyl-α-, -β-, or-γ-cyclodextrin having 2 to 15 hydroxypropyl groups per molecules of cyciodextrin, about 0 to about 6.0 weight percent (basis on antibiotic of Formula I, II, III) of a pharmaceutically acceptable non-ionic surfactant. The preferred pharmaceutically acceptable non-ionic surfactant, when used, is the sorbitan mono-9-octadecenoate poly (oxy-1,2-ethanediyl) derivative such as Tween-80, but any other non -ionic surfactant which produces pharmaceutically acceptable compositions, i.e., compositions which when dissolved in a pharmaceutically acceptable carrier are substantially free of haze, cloudiness and particulate matter as measured by standard analytical techniques, e.g., nephelometry. Particularly preferred compositions of matter of this invention contain 2.85 to 5.70% by weight of Tween-80 and a antibiotic compound of Formula III. "The preferred pharmaceutical composition of this invention contains the following: (a) the lipophilic oligosaccharide antibiotic represented by Formula III, (b) a base capable of forming a pharmaceutically acceptable salt with lypophilic oligosaccharide antibiotic of Formula III and (c) hydoxypropyl-α-, β- or-γcyclodextrin having about 2 to about 15 hydroxypropyl groups per molecule of said α-β and γ-cyclodextrin and wherein the molar ratio of (a):(b):(c) is 1:2–3:1–6."

BIOLOGICAL ACTIVITIES

We have surprisingly found that the preferred composition of matter of this invention, comprising one mole of the compound represented by Formula III 2 moles of NMG and 6 moles of 2-hydroxypropyl-βcyclodextrin having 7.4 hydroxypropyl groups per molecule of β-cyclodextrin, has substantially the same geometric mean MICs (GMM) against various bacteria, and substantially the same serum protein binding values as the compound of Formula III per se. It is expected that all the compositions of matter of this invention will behave similarly.

The in vitro antibacterial activity tests were performed via conventional agar dilution methods in Mueller—Hinton agar. The GMMs for the above-listed preferred composition of matter of this invention and for the compound of Formula III were determined against vadous bacteria, e.g., gram positive and gram negative bacteria. The term "susceptible gram positive and gram negative bacterial infections " means a broad range of gram positive bacterial infections. e.g., methicillin-resistant and methicillinsus-ceptible staphylococci, various strains of streptococci and enterococci and some gram negative bacterial infections, e.g., *E. coli* Klebsiella, Salmonella and Pseudomonas. The compound of Formula III had excellent activity (10-fold more potent than vancomycin) against both methicillin-resistant staphylococci (GMM, 0.1 µg/ml) and methicillin-susceptible staphylococci (GMM, 0.5 µg/ml). The compound of Formula III also had good activity (2-fold more potent than vancomycin) against *Enterococcus faecalis* (GMM, 0.49 µg/ml) and good activity (MICs, $\leq$0.5 µg/ml) against various strains of streptococci and enterococci resistant to vancomycin (MICs, $\geq$128 µg/ml). The compound of Formula III was very active against *Borrelia burgdorferi* (MICs, $\leq$0.49 µg/ml) and *Legionella pneumophila* and *L. longbeacheae* (MICs 2.5 µg/ml) but was only slightly active against gram-negative bacteria (GMM, $\geq$760 µg/ml), *Trichomonas vaginalis* (MICs, $\geq$192 µg/ml) and Mycoplasma sp. (MICs 200 µg/ml). No cross resistance with other antibiotics was observed.

The compound of Formula III had moderate bactericidal activity against various clinical and laboratory strains of staphylococci. The bactericidal activity of the compound of Formula III against staphylococci and enterococci was similar to that of vancomycin. The compound of Formula III had good activity against staphylococci in mice (PD$_{50}$ range 0.5 to 25.0 mg/kg), similar to that of vancomycin (0.7 to 28.5 mg/kg).

Following IV administration (30 mg/kg) of the compound of Formula III and 2 molecules of NMG, high serum levels were seen in rats (peak about 90 ug/ml) with a long serum beta half life.

The pharmaceutically acceptable compositions of matter of this invention are expected to be active against the above-listed susceptible bacteria as well as against. spirochetes including *Treponema pallidum*, anaerobes including *Clostridium difficile* as well as against Pneumocystis. Toxoplasma. protozoa and helminths.

Based on the activity of the compound of Formula III against *borrelia burgdorferi* and *Legionella pneumophila* and *L, longbeacheae*, expect that the compositions of matter containing the compound of Formula-III will exhibit activity in a human model against Lyme disease and iegionaire's disease.

The present invention provides a method of treating or preventing susceptible gram-posititive and gram-negative bacterial infections in animals by administering to such animals especially man afflicted with such infections an amount of a pharmaceutical composition of the compositions of matter of this invention and a pharmaceutically acceptable carrier therefor.

The compositions of matter of this invention may be combined with any pharmaceutically acceptable carrier, e.g., sterilized water, aqueous ethanol, vegetable oils, or polyols, e.g., polyethylene glycols and propylene glycol and administered orally, parenterally or topically in a valet of formulations. The use of sterilized water as a carrier is preferred. The sterilized water may optionally contain pharmaceutically acceptable substances, e.g. sodium chloride, potassium nitrate, glucose, mannitol, dextrose, sorbitol, xylitol or buffers such as phosphate, a Cetate or citrate as well as preservatives.

The compositions of matter of this invention are prepared by admixing a lipophilic oligosaccharide antibiotic of Formula I, II or III with at least about a stoichiometric amount of a base capable of forming a pharmaceutically acceptable salt thereof in a suitable solvent such as water. and with a specified amount of, for example hydroxypropyl-α-, -β- or -γ-cyclodextrin having about 2 to 15 hydroxypropyl groups per molecule of cyclodextrin. The order of admixing is not critical, but preferably an aqueous solution of the specific cyclodextrin is admixed with the base or alternatively it may be added after the base is admixed with the lipophilic oligosaccharide antibiotic. The formation of the aqueous solutions may take place at a temperature between 15° and 35° C. The aqueous solution so formed is filtered to produce a clear aqueous solution of the complex which may be evaporated or preferably freeze-dried to form the compositions of matter of this invention in the form of a lyophilized powder which is readily re-constituted by addition an amount of a pharmaceutically acceptable carrier such as water. The pharmaceutically acceptable non-ionic surfactant e.g. Tween -80when used, would be added to the aqueous solution before filtration and lyophilization. Alternatively, the aqueous solution may be frozen, thawed and thereafter filtered before use, e.g., as an IV formulation. It is a special feature of the present invention that the pharmaceutical compositions of the present invention form aqueous solutions and yet contain less than about 20 weight percent, preferably less than 10 and more preferably about 1.0 to 5.0 weight percent of an amount of hydroxypropyl-α-, -β- or -γ-cyclodextrin. The discovery that pharmaceutical compositions useful for safely and effectively delivering lipophilic oligosaccharide antibiotics to the serum of animals afflicted with susceptible bacterial infections, especially susceptible gram positive and gram negative bacterial infections, could be prepared by use of less than 20 weight percent. of for example hydroxypropyl-β-cyclodextrin is particularly surprising in view of the teachings of the Bodor U.S. Pat. No. 4,983,586 to use 20 to 50 weight percent of hydroxypropyl-β-cyclodextrin to avoid gelling or precipitation of drug and of the teaching of Pitha U.S. Pat. No. 4,727,064 to use 40 to 60 weight percent of hydroxypropyl-β-cyclodextrin to solubilize various drugs including salts of retinoic acid.

For oral administration, the compositions of this invention may be compounded in the form of tablets, capsules, elixers or the like. Tablets and capsules may contain such excipients as starch or lactose; liquid forms may contain coloring or flavoring agents. Topicals preparations may be in the form of creams, hydrophobic and hydrophylic ointments, or aqueous, non-aqueous or emulsion-type lotions as well as pessaries or powders. Typical carriers for such formulations are water, oils, greases, polyesters and polyols. Parenteral formulations, e.g., injectable dosage forms, are usually liquids such as solutions or suspensions, with typical carriers being distilled water and saline solution. Parenteral formulations are preferred. Intravenous (IV) formulations are more preferred.

The dose to be administered in any particular dosage form will depend upon various factors, such as the weight, age and sex of the animal especially a mammal such as a human being being treated, the susceptibility of the infecting organism to the lipophilic oligosaccharide antibiotic, the stage and severity of the infection. Generally, the dosage of the lipophilic oligosaccharide antibiotics of Formula I, II or III administered is from about 1.0 mg to about 15 mg per kilogram of body weight, preferably about 5 mg per kilogram of body weight per day in divided dosages, the specified dosage being left to the discretion of the practitioner; IV administration is preferred.

In treating certain patients with the compositions of this invention, it is possible to include other pharmaceutically active ingredients in the same dosage unit.

EXAMPLES

Example 1

A 100 liter fermentation of strain SCC 2146 of *Micromonospora carbonacea* var. *africana* NRRL 15099, ATCC 39149 improved as described hereinabove, was conducted in accordance with the procedures of Example 1B of U.S. Pat. No. 4,597,968 except that the following production medium (4l+½Ni) was used and that the fermentation was conducted at 34° C. for 24 hr followed by lowering the temperature to 30° C. for the duration of the fermentation run, i.e., for another 72 hr (total fermentation time of 96 hr). Aeration and agitation rates were, 0.35 vvm and 350 rpm, respectively

| Glucose | 2.2% (weight) |
|---|---|
| PDP 650 dextrin | 4.0% (weight) |
| Yeast Extract | 0.5% (weight) |
| Meat Peptone | 0.6% (weight) |
| Corn Steep Liquor | 0.5% (volume) |
| Nickel Chloride | $2.5 \times 10^{-6}$ M |
| Calcium Carbonate | 0.4% (by weight) |
| Tap Water q.s. to give | 1000 ml |

B. Isolation

Extract the fermentation broth of Example 1A twice with 200 L of ethyl acetate. Combine the ethyl acetate extracts and concentrate to provide a concentrated antibiotic complex containing a mixture of the compound of Formula III and the nitroso analog thereof (as determined by HPLC).

Example 2

A) To 919 g of antibiotic complex produced as described in Example I and containing 294 g (32%) of a mixture of 3.4 moles of the nitroso analog to one mole of the compound of Formula III dissolved in 4.6 L of ethyl acetate, 68.8 g of NaHCO₃ and 2.98 g of vanadyl acetylacetonate 3M in 2,2,4-trimethylpentane available-from Aldrich (0.06 eq); 394 mL of 3M tbutylhydroperoxide was added to the so-formed mixture after a ½ hour period. Portions of 1.45 g (0.03 eq) of vanadyl acetylacetonate were added thereto at 0 and after 1½, 2 ½, 3 ½ and 4 hours so that 0.15 eq of vanadyl acetylacetonate was added over 4 hours. The reaction mixture was immersed in an ice bath, and 203 mL (0.5 eg) of triethylphosphite $(C_2H_5O)_3P$ was added thereto. The so-formed reaction mixture was diluted with an equal amount of ethyl acetate while keeping the temperature of the reaction mixture at $\leq 30°$ C. The diluted ethyl acetate reaction mixture was washed twice with water. The aqueous layers were salted and extracted with ethyl acetate, The combined organic extracts were dried over MgSO₄, filtered and concentrated. The so-formed residue was dissolved in a minimum amount of acetone and precipitated into 7 L of 1:9 (v/v) ethyl ether/hexane. The residue was filtered and washed with hexane dried under vacuum and heat to give 928 g containing 30% (278 g) of the nitro compound of Formula III.

B) The residue of Example 2A was purified on 5 kg of silica gel in a column. The column was eluted with 12 liters of $CH_2Cl_2$ containing successively 10%, 20%, 25%, 30%, 35% (v/v) of acetone. The appropriate fractions were combined and concentrated at $\leq 35°$ C. The so-formed residue was dissolved in acetone and precipitated into 10 parts of 10% ethyl ether/hexane. The product was filtered and dried under vacuum without heat. The main fraction contained 147.5 g of the compound of Formula (98.7% pure). The other fractions contained crude product and were subjected to repeated silica gel chromatography until at least a 96–98% pure product was obtained. The structure was determined by NMR and MS and found to be consistent with that of Formula III.

Example 3A

An aqueous solution containing 23.97 mg of N-methyl glucamine ("NMG") and 570.90 mg of 2-hydroxypropyl -β-cyclodextrin ("HPβCD") having 7.4 hydroxypropyl groups per molecule of HPβCD was prepared in 5 mL of water.

To this solution was added 100 mg of the compound of Formula III. After mild agitation, a homogeneous complex containing 20 mg per mL of the compound of Formula III was formed. The molar ratios of the three components were 1 mole of the compound of Formula III to 2 moles of "NMG" to 6 moles of HPβCD. The so-formed solution Was filtered through a 0.45 µm membrane and freeze-dried and stored in a moisture-free environment. For preparation of a pharmaceutical composition, a pharmaceutically acceptable carrier such as water was added. Similar results were obtained using HPβCD having 3.9 to 7.5 hydroxypropyl groups per mole of β-cyclodextrin.

The formation of a clear aqueous solution of a homogeneous complex prepared in accordance with these procedure of this Example is verified by use of standard techniques, i.e., light scattering nephelometry and line width measurements in the proton NMR. The safe and effective administration of the pharmaceutical composition of clear aqueous solutions of the homogeneous complex prepared in accordance with the procedures of this invention was tested in various in-vivo animal models such are reported in Table 1–4.

Example 3B

The procedure of Example 3A is followed except that 1750 mg of HPβCD containing 7.4 hydroxpropyl groups per molecule was added to an aqueous solution of 126 mg of NMG and 350 mg of the compound of Formula III. The molar ratios of the three components in the homogeneous solution so-formed were 1 mole of the compound of Formula III to 3 moles of NMG to 5 moles of HPβCD. To this solution were added 500 mg of granular mannitol, USP grade and 10 mg of Polysorbate-80 (Tween-80) NF. The weight percent of Tween-80 is 2.85% basis the compound of Formula The so-formed solution was filtered and freeze-dried as described in Example 3A.

The freeze-dried composition is stored in vials in a moisturefree environment. For preparation of a pharmaceutical composition suitable for i.v. administration, 20 ml of sterile water is added.

Example 4

The following examples present the use of the NMR chemical microtitration technique for the determination of the equilibrium constants for complexing of the 2,4 dihydroxy 6-methyl phenyl ring (non-chloroaromatic) and for the 3,5-dichloro-2-methoxy-4-hydroxy 6-methyl phenyl ring (dichloroaromatic ring) of NMG salt of the compound of Formula III with 2-hydroxypropyl-β-cyclodextrin (HPCγCD) having 7.4 and 3.4 hydroxypropyl groups per mole of HPβCD and with 2-hydroxypropyl-γ-cyclodextrin ("HPγCD") having 4.4 hydroxypropyl groups per mole of HPγCD. The measurements were made using a Varian XL 400 at 400 mHz at 20° C.

A. A solution containing 10 mg of the compound of Formula III per ml of D$_2$O and 3 equivalents of N-methyl glucamine ("NMG") was prepared. To this solution was added mg portions of HPβCD having 7.4 hydroxypropyl groups per molecule of HPβCD. The change in chemical shifts of the 68 methyl group in the Formula III and 54 methylene protons in Formula III were measured as increasing amounts of HPβCD were added. The equilibrium constants for 50% complexation were calculated using standard techniques. The moles of HPβCD required to achieve 90% complexation or binding at both aromatic rings were also determined. The moles of HPβCD required to achieve 90% complexation at both aromatic sites was 6.6; 2 moles of HPβCD were required to achieve 50% complexation. The equilibrium constants are reported in the following Table 8.

B. The procedures of Example 4A were followed except that HPβCD having 3.4 hydroxypropyl groups per mole HPβCD was used. The results are reported in the following Table 8. The moles of HPβCD required to achieve 90% complexation at both aromatic sites was 6.6 mole.

C. The procedures of Example 4C were followed except that HPγCD having 4.4 hydroxypropyl groups per mole of HPγCD was used. The moles of HPγCD required to achieve 90% complexation at both site was 4.0; 1.4 moles were required to achieve 50% complexation. The results are reported in Table 8 below:

What is claimed is:

1. A composition comprising:

(a) a lipophilic oligosaccharide antibiotic represented by Formula I;

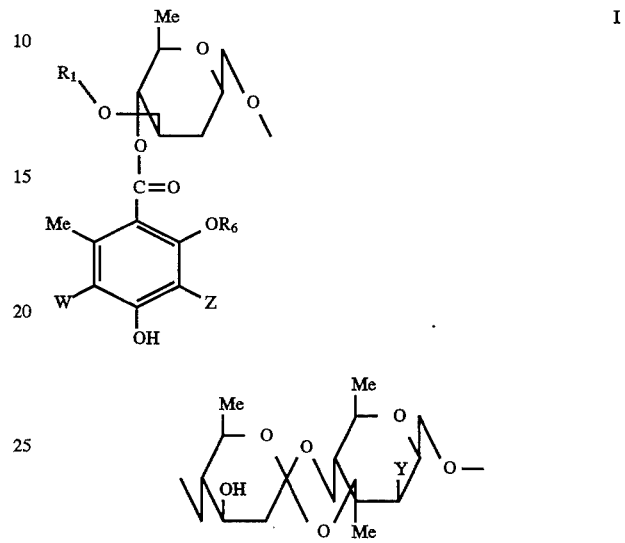

I

-continued

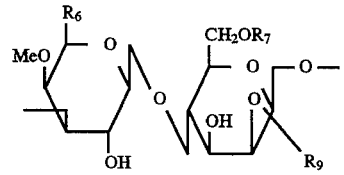

TABLE 8

| Equilibrium Constants (Liters/Mole) for Complexes of 1 mole of Compound III: 3 moles of NMG with HPβCD and HPγCD | | | |
|---|---|---|---|
| Complexation Site in compound III | HPβCD n$^1$ = 7.4 | HPβCD n$^1$ = 3.4 | HPγCD n$^2$ = 4.4 |
| Non-Chloro Aromatic Ring$^3$ | 183 ± 5 | 188 ± 5 | 355 ± 9 |
| $^3$DiChloro Aromatic$^4$ Ring | 953 ± 18 | 983 ± 34 | 315 ± 28 |

$^1$n = mean number of hydroxypropyl groups per molecule of HPβCD.
$^2$n = mean number of hydropropyl groups per molecule of HPγCD.

$^3$Non-Chloro Aromatic Ring in III =
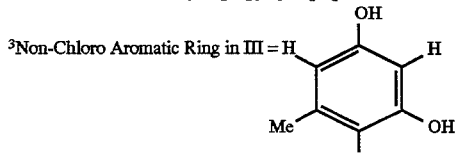

$^4$The Dichloro Aromatic Ring in III =
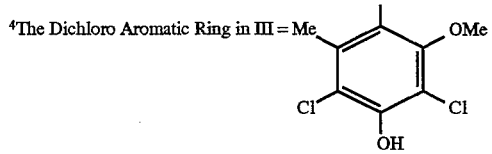

By use of the NMR chemical microtitration technique, the complexing amount of HPβCD having 7.4 hydroxypropyl groups per molecules of HPβCD required for one mole of the 3:1 NMG salt of the antibiotic of Formula III was determined to be 6.6 mole to achieve 90% complexation (at both aromatic groups in Formula III ) and to be 2 moles to achieve 50% complexation at both aromatic groups in Formula III.

-continued

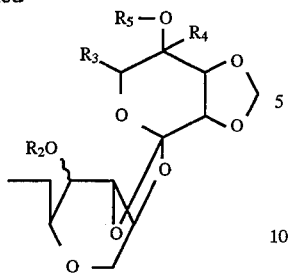

wherein

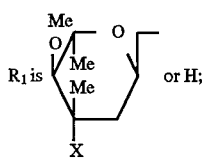

R₁ is [structure] or H;

X is one of $NO_2$, NO, $NH_2$, $NHCOCH_3$, NHOH, $NH(C_2H_5)$, $N(C_2H_5)_2$, OH or H;

$R_2$ is one of $CH_3$, $COCH(CH_3)_2$, $COCH_3$, $CO(CH_2)_3CH_3$, $COCH_2CH_3$ or H;

$R_3$ is $CH_3$ or H;

$R_4$ is one of $COCH_3$, $CH(OCH_3)(CH_3)$; $CH(OH)CH_3$, CHO, or H;

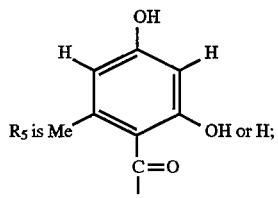

$R_5$ is Me [structure] OH or H;

$R_6$ is $CH_3$ or H;
$R_7$ is $CH_3$ or H;
$R_8$ is $CH_3$, $CH_2OH$ or H;
$R_9$ is $CH_3$ or H;
Y is OH, H or $CH_3$
W is Cl or H; and
Z is Cl or H;

(b) at least about a stoichiometric amount of a base capable of forming a pharmaceutically acceptable salt with a lipophilic oligosaccharide antibiotic of Formula I;

(c) a hydroxypropyl-α-β- or -γ-cyclodextrin wherein the average number of hydroxypropyl substituents on said -α, β- and γ-cyclodextrin is in the range of about 2 to about 15, and said amount is sufficient to achieve efficacious delivery of said lipophilic oligosaccharide antibiotic to the serum of an animal while simultaneously avoiding occurrence of adverse reaction syndrome; and (d) 0 to 6.0 by weight (basis an antibiotic of Formula I) of a pharmaceutically acceptable non-ionic surfactant.

2. The composition of claim 1 wherein the lipophilic oligosaccharide antibiotics represented by Formula I are selected from the group consisting of flambamycin, the everninomicins, the everninomicin-type antibiotics, curamycin, and the avilamycin A-N antibiotics.

3. A pharmaceutical composition for treating susceptible gram-positive and/or gram-negative bacterial infections comprising an antiinfective amount of a composition of claim 1 and a pharmaceutically acceptable carrier therefor.

4. The pharmaceutical composition of claim 3 wherein the base is N-methylglucamine.

5. A method of preventing adverse reaction syndrome in animals following parenteral administration of a lipophilic oligosaccharide antibiotic represented by Formula I of claim 1 while simultaneously delivering an antiinfective amount of a said antibiotic to said animal, said method which comprises parenterally administering to said animal an antiinfective amount of a composition of claim 1 together with a pharmaceutically acceptable carrier therefor.

6. A composition comprising (a) a compound represented by the Formula II

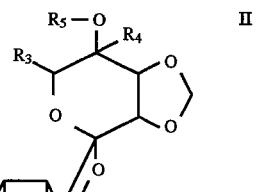

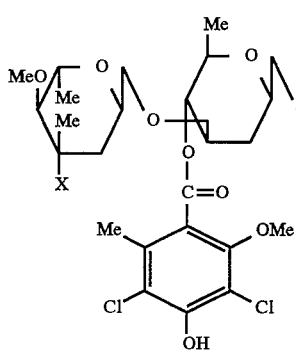

wherein

X is one of $NO_2$, NO, NHOH, $NH_2$, $NHCOCH_3$, $NH(C_2H_5)$, $N(C_2H_5)_2$, OH or H;

Y is OH, H or $CH_3$;

$R_2$ is H or $CH_3$;

$R_3$ is H;

$R_4$ is H or $CH(OCH_3)(CH_3)$; and $R_5$ is H or

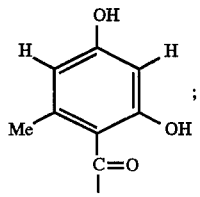

;

(b) at least about a stoichiometric amount of a base capable of forming a pharmaceutically acceptable salt with a compound of Formula II;

(c) an amount of hydroxypropyl-α-, -β- or -γ-cyclodextrin wherein the average number of hydroxypropyl substituents on said α, -β-and γ-cyclodextrin is in the range of about 2 to about 15, and said amount is sufficient to achieve efficacious delivery of said lipophilic oligosaccharide antibiotic to the serum of an animal while simultaneously avoiding occurrence of adverse reaction syndrome; and (d) 0 to 6.0% by weight (basis a compound of Formula II) of a pharmaceutically acceptable non-ionic surfactant.

7. A pharmaceutical composition for treating susceptible gram-positive and/or gram-negative bacterial infections comprising an antiinfective amount of a composition of matter of claim 6 and a pharmaceutically acceptable carrier therefor.

8. The pharmaceutical composition of claim 7 wherein the base is N-methylglucamine.

9. A method of preventing adverse reaction syndrome in animals following parenteral administration of a lipophilic oligosaccharide antibiotic represented by Formula II of claim 6 while simultaneously delivering an antiinfective amount of a said antibiotic to said animal, said method which comprises parenterally administering to said animal an antiinfective amount of a composition of claim 6 together with a pharmaceutically acceptable carrier therefor.

10. A composition comprising (a) the composition represented by Formula III

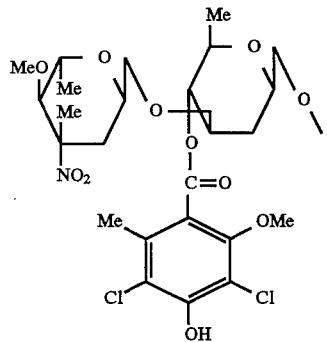

III

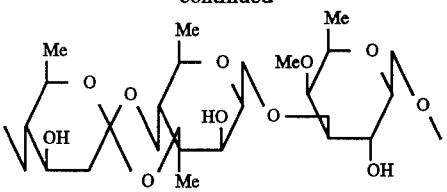

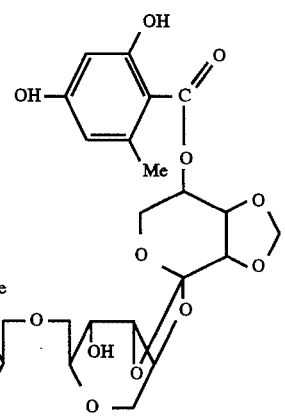

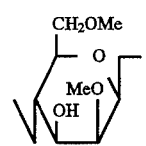

(b) at least about two equivalents of a base (per mole of the compound of Formula III) capable of forming a pharmaceutically acceptable salt with the compound of Formula III; (c) an amount of hydroxypropyl-α, -β- or γ-cyclodextrin having about 2 to about 15 hydroxypropyl groups per mole of said α-, β- and γ-cyclodextrin and wherein said amount is sufficient to achieve efficacious delivery of said lipophilic oligosaccharide antibiotic to the serum of an animal while simultaneously avoiding occurrence of adverse reaction syndrome; and (d)0 to 6.0% by weight (basis a compound of Formula III) of a pharmaceutically acceptable non-ionic surfactant.

11. A pharmaceutical composition for treating susceptible gram-positive and/or gram-negative bacterial infections comprising an antiinfective amount of a composition of claim 10 and a pharmaceutically acceptable carrier therefor.

12. A method of treating susceptible gram-positive and/or gram-negative bacterial infections in animals which comprises administering an amount of the pharmaceutical composition of claim 11 effective for such purpose.

13. The pharmaceutical compositions of claim 11 wherein the molar ratio of (a):(b):(c) is 1:2–3:1–6.

14. A method of preventing adverse reaction syndrome in animals following parenteral administration of a lipophilic oligosaccharide antibiotic represented by Formula III while simultaneously delivering an anti-infective amount of a said antibiotic to said animal, said method which comprises parenterally administering to said animal an anti-infective amount of a composition of claim 10 together with a pharmaceutically acceptable carrier therefor.

15. The composition of claim 10 wherein the base is selected from the group consisting of chloroprocaine, procaine, piperazine, glucamine, N-methylglucamine, N'N-dimethylglucamine, ethylenediamine, diethanolamine, diisopropylamine, diethylamine, N-benzyl-2-phenylethylamine, N,N'-dibenzylethylenediamine, choline, clemizole, tris(hydroxymethyl)aminomethane, D-glucosamine and sodium hydroxide.

16. The composition of claim 10 wherein the base is N-methylglucamine.

17. The composition of claim 10 wherein hydroxypropyl-β-cyclodextrin is used.

18. A composition of claim 10 which comprises a pharmaceutically acceptable non-ionic surfactant.

19. A composition of claim 18 wherein the pharmaceutically acceptable non-ionic surfactant is a sorbitan mono-9-octa-decenoate poly(oxy-1,2-ethanediyl) derivative.

20. A composition of claim 10 which further comprises manitol.

21. A composition which comprises:

(a) the compound represented by Formula III:

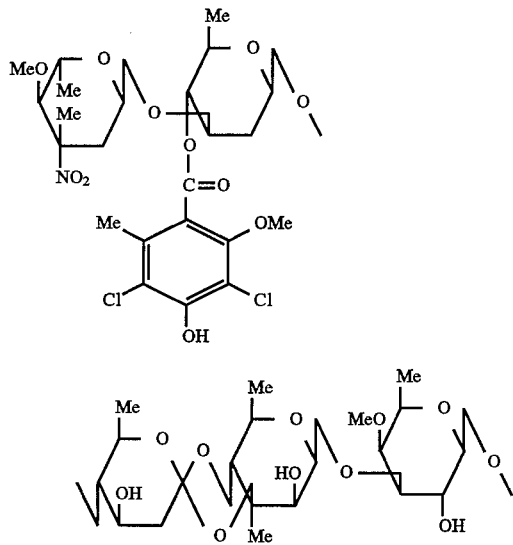

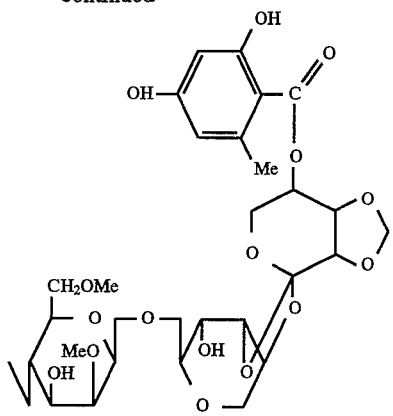

(b) N-methylglucamine;

(c) hydroxyprophyl-β-cyctodextrin containing 7.4 hydroxypropyl groups per molecule;

(d) the sorbitan mono-9-octa-decenoate poly(oxy-1,2-ethanediyl) derivate, polysorbate 80; and (e) manitol;

wherein the molar ratio of (a):(b):(c) is 1:3:5 and the weight percent of the polysorbate 80 (basis the compound of formula III) is about 2.85% of and the weight percent of manitol (basis whole composition) is about 18.28%.

22. A method of treating susceptible gram-positive and/or gram negative bacterial infections in animals which comprises administering an amount of the composition of claim 21 effective for such treating.

* * * * *